United States Patent [19]

O'Neill

[11] 4,088,135
[45] May 9, 1978

[54] BALLOON CATHETER WITH COAXIAL ACTIVATING SYRINGE

[75] Inventor: William J. O'Neill, Milltown, N.J.

[73] Assignee: Victory Engineering Corporation, Springfield, N.J.

[21] Appl. No.: 757,660

[22] Filed: Jan. 7, 1977

[51] Int. Cl.² .......................................... A61M 25/00
[52] U.S. Cl. ................................ 128/348; 128/349 B
[58] Field of Search ............ 128/348, 349 B, 349 BV, 128/350 R, 351, 129, 246, 325, 344

[56] References Cited

U.S. PATENT DOCUMENTS

| 3,211,150 | 10/1965 | Foderick | 128/349 BV |
| 3,211,151 | 10/1965 | Foderick et al. | 128/349 B |
| 3,978,863 | 9/1976 | Fettel et al. | 128/348 |
| 3,995,623 | 12/1976 | Blake et al. | 128/349 R X |
| 4,000,741 | 1/1977 | Binard et al. | 128/349 BV |

FOREIGN PATENT DOCUMENTS 2,313,084  12/1976  France .............................. 128/349 B Primary Examiner—Dalton L. Truluck
Attorney, Agent, or Firm—Albert F. Kronman

[57] ABSTRACT

A balloon catheter having a flexible tubing containing a plurality of lumens and an inflatable balloon adjacent its distal end is connected to a coaxial unit incorporating a syringe at its proximal end. The syringe applies fluid through at least one of the lumens to inflate the balloon. Other lumens are connected to fluid sources or electrical leads through the coaxial unit for diagnostic or medicinal purposes. Visual means carried by the syringe indicate balloon failure.

7 Claims, 5 Drawing Figures

U.S. Patent May 9, 1978 4,088,135
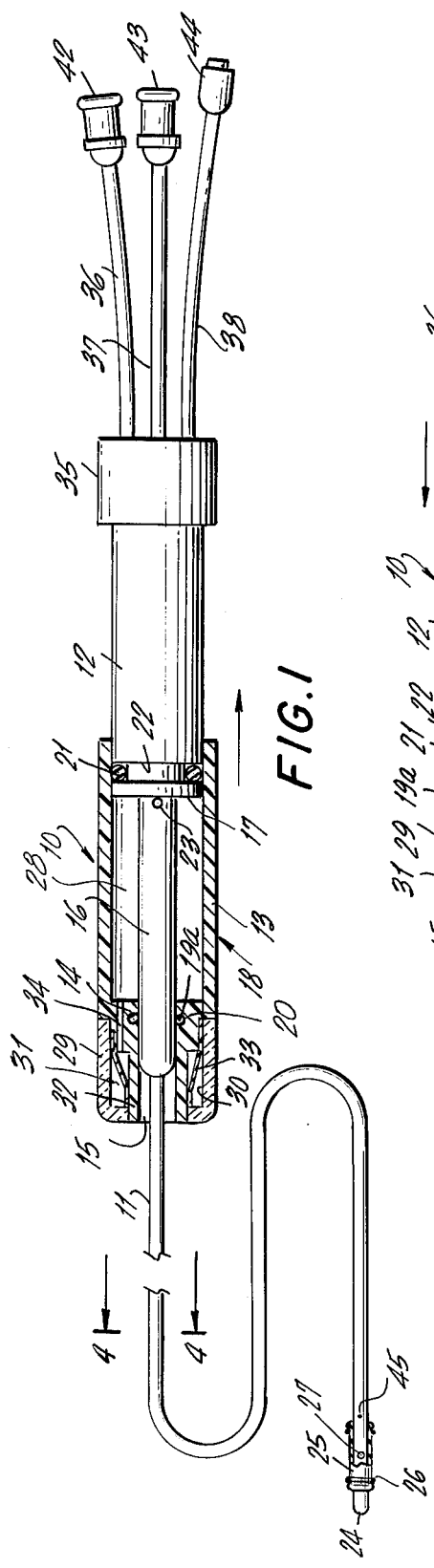
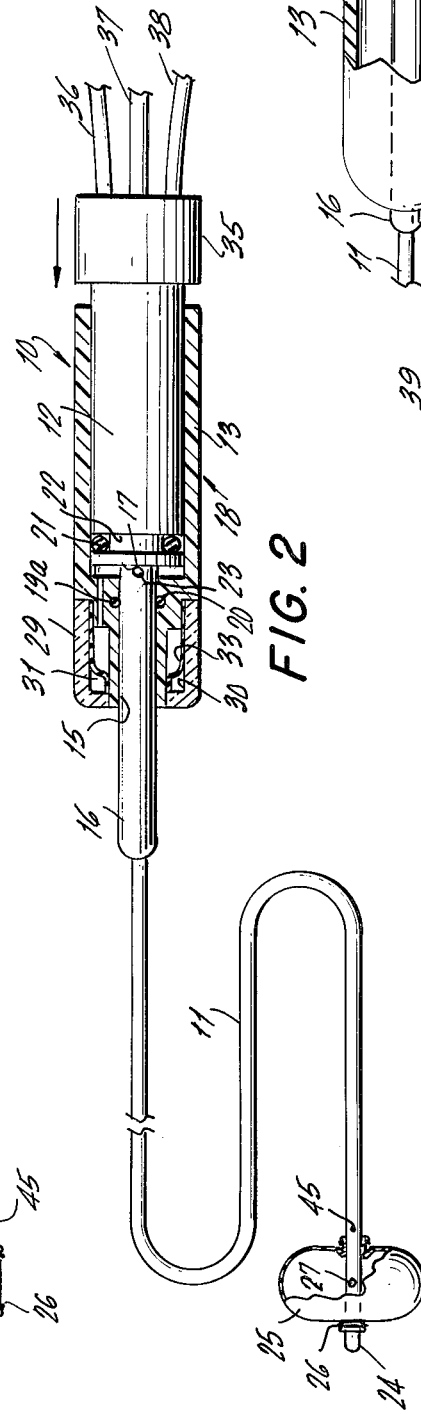
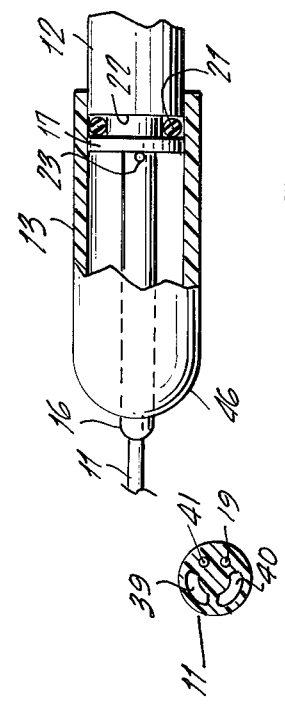
FIG. 1
FIG. 2
FIG. 3
FIG. 4
FIG. 5

BALLOON CATHETER WITH COAXIAL ACTIVATING SYRINGE

BACKGROUND OF THE INVENTION

Catheters of the balloon type having long flexible tubing to reach the desired areas are well-known, as shown in U.S. Pat. Nos. 3,448,739; 3,409,015 and 3,923,065. Such prior art devices employ "Y" shaped fittings or branched tubing at the proximal end of the flexible tubing making them inconvenient to handle and bulky. In addition, once inserted and inflated, failure of the balloon due to leaks or bursting could not be detected readily.

The present invention seeks to overcome the difficulties experienced with prior art devices by providing a small coaxial unit at the proximal end of the flexible tubing which is light in weight and easy to use, particularly in such applications as flow directed catheters. The balloon inflating syringe forms the major portion of the coaxial unit which may also contain a visible balloon pressure indicator. Instead of the branched contruction of prior art devices, all connections are made through the end of the body portion of the coaxial unit. The device lends itself to a wide variety of catheter uses.

SUMMARY

The catheters shown and described herein comprise an elongated flexible tube containing a plurality of longitudinal passages or lumens. The lumens communicate with openings in the tube at or near the distal end thereof for the application of balloon inflating fluid, chemicals, or temperature sensing devices. Fluids, chemicals and electrical wires are led into the lumens through a coaxial unit at the proximal end of the tubing. A sleeve, slidably received upon the body of the coaxial unit, cooperates therewith to form a syringe to inflate or deflate a balloon on the distal end of the tube. The sleeve also carries therein a small flexible membrane which is inflated by the fluid pressure applied to the balloon. The membrane is visible through the sleeve wall to indicate the condition of the balloon.

FIGURES

In the accompanying drawing forming part hereof, similar parts have been given the same reference numerals, in which drawing;

FIG. 1 is a view in side elevation, party broken away, of a complete embodiment of a catheter made in accordance with the present invention.

FIG. 2 is a view similar to FIG. 1 showing the catheter when the balloon is inflated.

FIG. 3 is a view in side elevation of the coaxial unit shown in FIG. 2.

FIG. 4 is a cross-sectional view, somewhat enlarged taken on line 4—4 in FIG. 1.

FIG. 5 is a fragmentary view, partially broken away of a coaxial unit comprising another embodiment of the present invention.

DETAILED DESCRIPTION

Referring to the drawing and particularly FIGS. 1-4, there is shown a catheter 10, made in accordance with the present invention, comprising an elongated flexible tube 11, a cylindrical body 12 and a sleeve 13 slidably received upon the cylindrical body. The tube 11 is preferably made of vinyl, polyetheylene, silicone rubber or the like.

An end wall 14 is provided in the sleeve opposite the cylindrical body 12. The end wall is centrally bored as indicated at 15 to receive therethrough one end of a guide stem 16. The opposite end of the guide stem is carried by the inner end of the cylindrical body and may be integral therewith. Both the guide stem and body are coaxially bored to receive the proximal portion of the flexible tube 11 in fluid tight engagement. The guide stem and cylindrical body 12 are made of a suitable rigid plastic material such as Nylon, Delrin or any other machinable plastic.

The end of the cylindrical body 12 within the sleeve 13 serves as the piston 17 of a syringe which directs fluid, either liquid or gas into the lumen 19 (best shown in FIG. 4) of the flexible tube 11. A small "O" ring 19a held in a recess 20 in the end wall 14 surrounds the guide stem 16 to provide fluid tight integrity at the front of the syringe 18 and a second "O" ring 21 is carried in a groove 22 in the cylindrical body 12 to prevent fluid from escaping from the syringe around the cylindrical body.

A small bore 23 is provided in the wall of the guide stem 16 adjacent the end of the cylindrical body 12. The bore 23 is in communication with the lumen 19 within the flexible tube 11.

The distal end 24 of the flexible tube 11 serves to support a balloon 25 which may be secured to the flexible tube by winding 26 at each end thereof or by cementing. A small bore 27 in the flexible tube 11 leads from the lumen 19 to the interior of the balloon 25. Thus as the sleeve 13 of the syringe 18 is pressed upon the cylindrical body 12, the fluid within the sleeve chamber 28 will be forced through the bore 23, the lumen 19 and out of the bore 27, to inflate the balloon 25 as shown in FIG. 2. When the sleeve 13 is moved in the opposite direction the fluid will be pulled back into the chamber 28 and the balloon will return to its original deflated condition.

In the embodiment shown in FIGS. 1-4, the distal end of the sleeve 13 is provided with a translucent plastic thimble 29 having a frosted inner surface 30. The thimble is coaxially bored to receive a protruding portion 32 of the end wall 14. The thimble 29 is also cemented to the sleeve 13 and end wall 14 to provide a fluid tight chamber 31 between the end wall 14 and the interior of the thimble.

A small membrane 33 is disposed within the thimble chamber 31. The membrane which is sleeve shaped, is secured at one end to the protuding portion 32 of the cylindrical body and at its opposite end between the sleeve 13 and the adjacent portion of the said body. As shown in FIGS. 1 and 2, the membrane 33 thus divides the thimble chamber 31 into two compartments. When there is no fluid pressure within the chamber the membrane is somewhat diagnally disposed across the chamber 31, as shown in FIG. 1. When the thimble 13 is urged upon the cylindrical body 12, pressure is applied through a small duct 34 in the end wall 14 against the membrane 33. The membrane will stretch and assume the position shown in FIG. 2 in which it is flattened against a portion of the inner surface 30 of the thimble 29. Since the membrane is formed of some suitable dark colored flexible material such as rubber, neoprene or a silicone rubber, it will be visible through the translucent thimble when in the inflated position. If the pressure against the membrane decreases, it will relax and tend to its original position as shown in FIG. 1. It will be apparent that any failure of the balloon 25, following inflation, can be detected by observing the condition of membrane 33 within thimble 24.

The cylindrical body 12 is provided with a boss 35 on the proximal end. The boss 35 serves as a stop for the sleeve 13 and facilitates handling of the catheter. The cylindrical body 12 is initially a hollow member to permit the proximal end of the flexible tube 11 to be pulled therethrough.

The flexible conduits 36, 37, 38 are secured to the flexible tube 11 within the cylindrical body 12 in communication with the lumens, 39, 40, 41 (see FIG. 4). The conduits are provided with connectors 42, 43, 44, which in turn are coupled to sources of chemicals, instruments or pumps for taking samples (not shown). Where instruments are used such as a temperature measuring device, a thin wire may be passed through the lumen 41 and connected at its distal end to a temperature sensitive component such as a thermistor 45 and at its other end to a device having a circuit and meter (not shown) for displaying temperature changes.

When the conduits 36 37, 38, are properly secured to the flexible tube 11, as described above, the hollow cavity in the cylindrical body 12 is filled with a suitable casting material such as an epoxy to rigidly secure all of the parts in place. Various external units such as are used in the medical profession and well known in the art may be added, interchanged or substituted for those described herein and coupled to the catheter 10 by means of the connectors 42, 43, 44.

Referring to the FIG. 5, there is shown another embodiment of the present invention in which the pressure indicating membrane 33 is omitted. In this form, the distal end 46 of the cylindrical body 12 is opaque and the thimble 29 is omitted. The small "O" ring 19a provides a fluid seal around the guide stem 16. In all other respects the construction of the catheter in FIG. 5 corresponds to that shown in FIG. 1-4.

From the foregoing it will be seen that there have been provided balloon catheter assemblies which are compact, easy to handle, light in weight and lend themselves to a wide variety of surgical requirements. Visible indications of the condition of the balloon at all times may also be incorporated in these structures.

The volume contained within the sleeve chamber 28 is of a size which will contain enough fluid to inflate the balloon 25 within its limits without causing normal balloon failure, as the sleeve 13 is pressed upon cylindrical body 12.

Having thus fully described the invention what is desired to be claimed and secured by Letters Patent is:

1. A balloon catheter assembly comprising a body, a sleeve slidably carried upon the body, an end wall at the distal end of the sleeve, an elongated hollow guide stem carried by the distal end of the body and extending coaxially therefrom and through the said end wall, an elongated flexible tube coaxially coupled at its proximal end to the hollow stem a plurality of lumens in said tube, sealing means carried within the sleeve to form a fluid tight chamber between the end wall and the distal end of the body, a plurality of conduits secured at one end within the body in communication with the lumens, connectors carried upon the free ends of the conduits, a balloon secured to the flexible tube spaced from the distal end thereof, openings in the wall of the said tube and in the said stem in communication with one of the said lumens to provide a continuous fluid path from the sleeve chamber to the interior of the balloon, and openings in the elongated flexible tube at the distal portion thereof in communication with one or more of the lumens in said tube.

2. A balloon catheter according to claim 1 in which the sealing means is disposed around the guide stem.

3. A balloon catheter according to claim 1 in which at least one of the lumens contains an electrical wire and at least one of the connectors is coupled to said wire.

4. A balloon catheter according to claim 1 in which the sleeve end wall is the form of a centrally bored block having a reduced portion on the distal end thereof, a centrally bored thimble is supported on the sleeve overlying the said end wall to form a chamber around the end of said end wall, said thimble being adapted to receive the guide stem therethrough, a membrane secured between the thimble and the end wall to divide the thimble chamber into two fluid tight compartments and a duct in the end wall connecting the sleeve chamber with the thimber chamber.

5. A balloon catheter according to claim 4 in which the membrane is formed of a substantially opaque resilient material and the thimble is formed of a translucent material.

6. A balloon catheter according to claim 5 in which the sleeve sealing means includes an "O" ring disposed around the body, spaced from the distal end thereof and in frictional contact with the inner surface of the sleeve.

7. A balloon catheter according to Claim 1 in which the end wall and the distal end of the body encloses a fluid tight chamber which is of a volume no greater than the desired volume of fluid to be applied to the balloon.

* * * * *